United States Patent
Mantegani et al.

(10) Patent No.: US 6,316,451 B1
(45) Date of Patent: Nov. 13, 2001

(54) HETEROCYCLYL ANTHRACYCLINONE DERIVATIVES

(75) Inventors: Sergio Mantegani; Gabriella Traquandi, both of Milan; Tiziano Bandiera, Gamboló Pavia; Jacqueline Lansen; Mario Varasi, both of Milan, all of (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 09/623,859
(22) PCT Filed: Mar. 4, 1999
(86) PCT No.: PCT/EP99/01544
  § 371 Date: Sep. 26, 2000
  § 102(e) Date: Sep. 26, 2000
(87) PCT Pub. No.: WO99/46253
  PCT Pub. Date: Sep. 16, 1999

(30) Foreign Application Priority Data

Mar. 10, 1998 (GB) .................................................. 9805082

(51) Int. Cl.⁷ ...................... C07D 277/42; C07D 233/88; A61K 31/425; A61K 31/415; A61P 25/28
(52) U.S. Cl. .................. 514/254.02; 514/235.8; 514/236.8; 514/326; 514/341; 514/254.04; 514/370; 132/133; 132/367; 132/370; 209/210; 209/270.7; 209/274.1; 193/314.7
(58) Field of Search ...................... 544/132, 133, 544/367, 370; 546/209, 210, 270.7, 274.1; 548/193, 314.7; 514/254.02, 254.05, 235.8, 236.8, 326, 341, 342, 370, 397

(56) References Cited

U.S. PATENT DOCUMENTS

| | | | |
|---|---|---|---|
| 5,637,572 | 6/1997 | Merlini et al. | 514/34 |
| 5,731,313 | 3/1998 | Suarato et al. | 514/255 |
| 5,985,887 | 11/1999 | Caruso et al. | 514/238 |
| 5,998,615 | 12/1999 | Suarato et al. | 544/154 |
| 6,096,888 | 8/2000 | Surato et al. | 514/154 |
| 6,103,700 | 8/2000 | Bandiera et al. | 514/34 |

FOREIGN PATENT DOCUMENTS

| | | | |
|---|---|---|---|
| WO-96/04895 | * | 2/1996 | (WO) . |
| WO-96/07665 | * | 3/1996 | (WO) . |
| WO-97/06165 | * | 2/1997 | (WO) . |
| WO-97/49433 | * | 12/1997 | (WO) . |

* cited by examiner

Primary Examiner—Deborah C. Lambkin
Assistant Examiner—Andrea M. D'Souza
(74) Attorney, Agent, or Firm—Oblon, Spivak, McClelland, Maier & Neustadt, P.C.

(57) ABSTRACT

A compound of formula (1) wherein $R_1$ is hydrogen, hydroxy, a group of formula $OR_5$ wherein $R_5$ is $C_1$–$C_6$ alkyl, $C_2$–$C_6$ alkenyl or $C_3$–$C_8$ cycloalkyl, halogen, amino which may be unsubstituted or mono or disubstituted by $C_1$–$C_6$ alkyl, $C_2$–$C_6$ alkenyl, aralkyl, acyl or trifluoroacetyl; $R_2$ is hydrogen, hydroxy, a group $NR_6R_7$ wherein $R_6$ and $R_7$ independently represent hydrogen, an optionally substituted $C_1$–$C_6$ alkyl, $C_2$–$C_6$ alkenyl, $C_3$–$C_8$ cycloalkyl or, taken together with the nitrogen atom, represent an optionally substituted $C_3$–$C_8$ heterocyclic ring; $R_3$ is hydrogen, hydroxy, $R_4$ is a 2-substituted thiazolyl or imidazolyl system and the pharmaceutically acceptable salt thereof, is useful in the treatment of amyloidosis. Processes for the preparation and pharmaceutical compositions are also described.

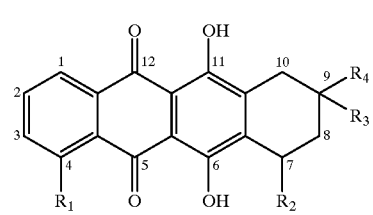

(1)

9 Claims, No Drawings

HETEROCYCLYL ANTHRACYCLINONE DERIVATIVES

This application is a National Stage of International Application PCT/EP99/01554, filed Mar. 4, 1999, which claims priority to GB 9805082.6, filed Mar. 10, 1998.

The present invention relates to 9-heterocyclyl anthracyclinone derivatives, to their use for the treatment of amyloidoses, to methods for their preparation and to pharmaceutical compositions containing them. More particularly, the present invention provides anthracyclinone derivatives which are characterized by the presence of a penta-atomic heterocyclic system linked to the position 9 of the anthracyclinone system and that are represented by the general formula 1

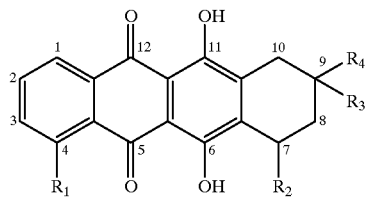

1 wherein:
$R_1$ is selected from:
  hydrogen,
  hydroxy,
  a group of formula $OR_5$ wherein $R_5$ is $C_1$–$C_6$ alkyl, $C_2$–$C_6$ alkenyl or $C_3$–$C_8$ cycloalkyl,
  halogen,
  and amino which may be unsubstituted or mono or disubstituted by $C_1$–$C_6$ alkyl, $C_2$–$C_6$ alkenyl, aralkyl, acyl or trifluoroacetyl;
$R_2$ is selected from:
  hydrogen,
  hydroxy, and
  a group $NR_6R_7$ wherein $R_6$ and $R_7$ independently represent hydrogen, an optionally substituted $C_1$–$C_6$ alkyl, $C_2$–$C_6$ alkenyl, $C_3$–$C_8$ cycloalkyl or, taken together with the nitrogen atom, represent an optionally substituted $C_3$–$C_8$ heterocyclic ring;
$R_3$ is selected from:
  hydrogen and
  hydroxy;
$R_4$ is a 2-substituted thiazolyl or imidazolyl system of formula A:

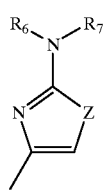

A wherein z represents sulfur or nitrogen and $R_6$ and $R_7$ are as defined above, and the pharmaceutically acceptable salt thereof.

The term "alkyl" as used herein includes both straight and branched chain radicals of up to 6 carbons, for example methyl, ethyl, propyl, butyl, pentyl, hexyl and the various branched chain isomers thereof, as well as straight and branched chain radicals optionally carrying one or more substituents selected from aryl, cycloalkyl, halogen, trifluoromethyl, hydroxy, alkoxy, aralkoxyl, amino, mono or dialkylamino, carboxy.

The term "alkenyl" as used herein includes both straight and branched chain radicals of up to 6 carbons such as, for example, allyl, butenyl, pentenyl, hexenyl, optionally sub-situted as the alkyl groups above.

The term "cycloalkyl" as used herein means a cycloalkyl group having 3 to 8 carbons, for example cyclopropyl, cyclobutl, cyclopentyl, cyclohexyl, cycloheptyl and cyclooctyl, optionally subsituted as the alkyl groups above.

The term "aryl" as used herein includes both monocyclic or bicyclic aromatic groups containing from 6 to 10 carbons in the ring portion such as phenyl or naphthyl, optionally substituted by one or more substituents selected from $C_1$–$C_6$ alkyl, $C_1$–$C_6$ alkoxyl, trifluoromethyl, halogen or hydroxy.

The term "heterocyclyl" as used herein is a 3- to 7-membered, saturated or unsaturated heterocyclic ring containing at least one heteroatom selected from N, O and S and which is optionally fused to a second 5- or 6-membered, saturated or unsaturated heterocyclic ring or to an aryl ring, optionally substituted by one or more substituents selected from $C_1$–$C_6$ alkyl, $C_1$–$C_6$ alkoxyl, trifluoromethyl, halogen or hydroxy.

The term "halogen" as used herein means fluorine, chlorine, bromine and iodine.

The term "aralkyl" as used herein refers to alkyl groups as previously defined having an aryl substituent, for example benzyl, phenethyl, diphenylmethyl and triphenylmethyl.

The term "alkoxyl" or "aralkoxyl" as used herein includes any of the above alkyl, cycloalkyl or aralkyl groups linked to an oxygen atom.

The term "acyl" as employed herein includes alkyl, aryl and heterocyclyl as described above linked to a carbonyl group.

This invention also includes all the possible isomers and mixture thereof, including diastereoisomeric mixtures and racemic mixtures, resulting from the possible combination of (R) and (S) stereochemistry at position 9 and, when substituents are present, at position 7. The present invention also provides the salts of those compounds of formula 1 that have salt forming groups, such as an acidic or a basic group (e.g. an amino group).

The salts are physiologically tolerable salts. In the case of compounds containing a basic amino group, the salts are formed with suitable inorganic or organic acids Inorganic acids are, for example, hydrochloric or sulfuric acid. Organic acids comprise mono-, di- and tricarboxylic acids, such as acetic, trifluoroacetic, tartaric and citric acid, or sulfonic acids like, for example, methansulfonic, trifluoromethansulfonic or p-toluensulfonic acid.

Preferred compounds of formula 1 are those wherein:
$R_1$ is selected from:
  hydrogen,
  hydroxy and
  methoxy;
$R_2$ is selected from:
  hydrogen,
  hydroxy and
  a group of formula $NR_6R_7$, wherein one or both of $R_6$ and $R_7$ represent hydrogen, methyl, ethyl, propyl, butyl, dimethylaminoethyl, dimethylaminopropyl, or taken together, represent 4-morpholinyl, 4-methylpiperazinyl, 4-phenylpiperazinyl, 1-piperidinyl, 1-pyrrolidinyl, 1,2,3,6-tetrahydropyridinyl;

$R_3$ is selected from:
hydrogen and
hydroxy;

$R_4$ is a 2-substituted thiazolyl or imidazolyl system as above defined.

Compounds of formula 1 as defined above can be prepared by (a) reacting a compound of formula 2,

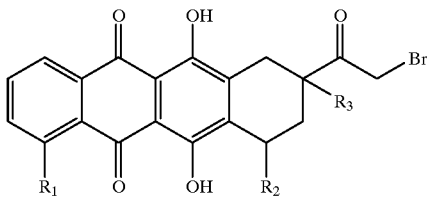

2 wherein $R_1$ and $R_3$ are as defined above and $R_2$ is hydrogen or hydroxy, with a compound of formula 3 or 7,

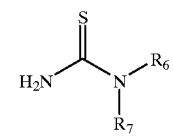

3

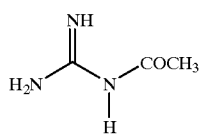

7 wherein $R_6$ and $R_7$ are as defined above, and if necessary, hydrolysing the resultant compound and (b) converting the resultant compound of formula 1 into a different compound of formula 1 by appropriate chemical reactions, such as alkylation, reduction, condensation/substitution.

In particular, the compounds of formula 1 wherein Z represents sulfur may be obtained by reacting a compound of formula 2 with a compound of formula 3 as above defined, analogously to the procedure described in the literature (see, for instance, *The Chemistry of Heterocyclic Compounds*, A. Weissberger Ed., John Wiley & Sons, 1979, vol. 34/1, p. 165; or Houben-Weyl, *Methoden der Organischen Chemie*, vol. E 8b, Georg Thieme, 1995).

The solvent is a proper organic solvent such as methanol, ethanol, dioxane or dimethylformamide. The reaction is carried out for a period of 1 to 24 hours at a temperature ranging from room temperature to 100° C. Preferably the solvent is a 1:1 mixture of ethanol and dioxane.

Compounds of formula 1 in which Z represents nitrogen can be prepared by reacting a compound of formula 2 with a compound of formula 7 as above defined, as described in the literature (see: T. L. Little and S. E. Webber *J. Org. Chem.* 1994, vol. 59, p. 7299).

The solvent is a proper organic solvent such as methanol, ethanol, acetonitrile, dioxane or dimethylformamide. The reaction is carried out for a period of 1 to 24 hours at a temperature ranging from room temperature to 100° C. Preferably the solvent is dimethylformamide and the reaction is carried out at room temperature. The resulting intermediate 2-acetylamino-imidazoles of formula 8

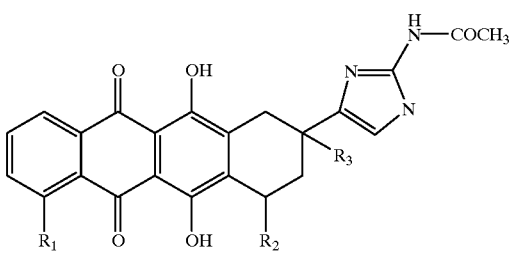

8 wherein $R_1$, $R_2$ and $R_3$ are as defined above are then hydrolized and the resultant compound of the formula 1 wherein $R_6$ and $R_7$ are hydrogens can be converted into different compounds of the formula 1 by alkylation. According to other conversion reactions of step b), a compound of formula 1, wherein $R_1$, $R_2$, $R_3$ and $R_4$ are as defined above, can also be converted into a different compound of formula 1 by appropriate chemical reactions described for the anthracyclines and anthracyclinones(see: F. Arcamone, *Doxorubicin Anticancer Antibiotics*, Medicinal Chemistry, a series of monographs, vol. 17, Academic Press, 1981) or by general synthetic procedures (see: J. March, *Advanced Organic Chemistry*, IV Ed., J. Wiley & Sons, 1992). Compounds of formula 1 in which $R_1$, $R_3$ and $R_4$ are as described above and $R_2$ is hydrogen are prepared by reacting the corresponding compounds where $R_2$ is an hydroxyl group with a reducing agent such as sodium dithionite in a proper solvent at room temperature. Preferably, the solvent is a 1:1 mixture of water and dimethylformamide.

Compounds of formula 1 in which $R_1$, $R_2$ and $R_4$ are as defined above and $R_2$ is $NR_4R_7$, wherein $R_6$ and $R_7$ are as defined above, are prepared by reacting compounds of formula 1, wherein $R_1$, $R_3$ and $R_4$ are as defined above and $R_2$ is a hydroxyl group, with an excess of ethylchloroformate in analogy to a procedure reported in the literature (see: L. Bernardi et al., *Il Farmaco Ed. Sc.* 1979, vol. 34, p. 884). The solvent is preferably pyridine or methylene chloride and the reaction is carried out at a temperature ranging from room temperature to 40° C. for a period of 1 to 6 hours. The resultant compound of formula 9

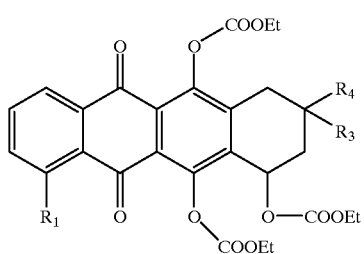

9 wherein $R_1$, $R_3$ and $R_4$ are as defined above, is then reacted with a compound of formula 5,

5 wherein $R_6$ and $R_7$ are as defined above. The solvent is a proper organic solvent such as methanol, acetonitrile, methylene chloride, tetrahydrofuran, dimethylformamide or a mixture of them and the reaction is carried out at a temperature ranging from room temperature to 50° C. for a period of 6 to 24 hours.

A compounds of formula 1 obtained according to the procedures reported before can be transformed into pharmaceutically acceptable salts thereof by dissolving the free base in a proper organic solvent like dichloromethane, methanol, ethanol or dioxane and adding a solution of a pharmaceutically acceptable inorganic or organic acid in methanol, ethanol or dioxane. The resulting salt of compound 1 is obtained by evaporation or concentration of the salt solution or the salt is precipitated by addition of diethyl ether to the salt solution.

Compounds of formula 2, wherein $R_1$ and $R_3$ are as defined above and $R_2$ is hydrogen or hydroxyl, are prepared starting from anthracyclinones of formula 4,

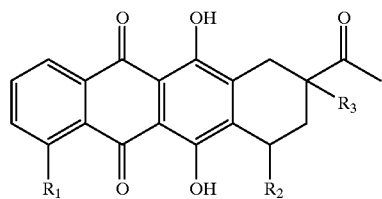

wherein $R_1$, $R_2$ and $R_3$ are as defined above, as described in the literature (see: T. H. Smith et al., *J. Org. Chem.* 1977, vol. 42, p. 3653).

Compounds of formula 4, wherein $R_1$, $R_2$ and $R_3$ are as defined above, may be prepared, depending on the nature of the substituents, starting from known anthracyclinones by appropriate chemical modifications as reported in the literature (see: F. Arcamone, *Doxorubicin Anticancer Antibiotics*, Medicinal Chemistry, a series of monographs, vol. 17, Academic Press, 1981).

Compounds of formula 3 are prepared by a two step reaction in analogy to a known procedure described in the literature (see, for example, H. Hartmann and I. Reuther *J. fuer Praktische Chemie* 1973, vol. 315, p. 144). Accordingly, by reacting a compound of formula 5 as defined above, with benzoyl isothiocianate (PhCONCS), a compound of formula 6,

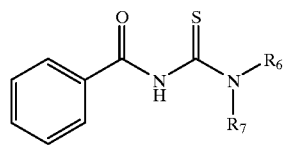

wherein $R_6$ and $R_7$ are as defined above, is obtained. The solvent is a proper organic solvent such as ethanol, methanol, acetone, dimethylformamide or pyridine. The reaction is carried out for a period of 1 to 5 hours at a temperature ranging from 0° C. to room temperature.

A compounds of formula 6 is then subjected to hydrolysis with an inorganic base, typically sodium hydroxide or potassium hydroxide, to give a desired compound 3 as defined above. The base is used in a 2- to 4-fold excess with respect to compound 6. The solvent is a mixture of water and a proper organic solvent such as methanol, ethanol or dioxane. The reaction is carried out for a period of 1 to 24 hours and at a temperature ranging from room temperature to 100° C.

The compounds of the present invention are characterized by inhibitory activity on the formation of amyloid deposits by amyloidogenic proteins and are able to induce the degradation of existing amyloid deposits.

The term amyloidoses indicates a group of diseases whose common characteristic is the presence, in the extracellular space, of amyloid deposits. Amyloidogenic proteins are proteins that have the tendency to aggregate and precipitate as amyloid. Proteins that precipitate as amyloid are both normal proteins, or truncated forms thereof, and mutated proteins, where one or more of the amino acid residues occurring at certain positions of the normal protein sequence are replaced by a different amino acid. Amyloid deposits are composed of insoluble fibrils, also referred to as amyloid fibrils. Amyloid fibrils cause cellular degeneration and organ failure that, in turn, result in different pathologies depending on the tissues and organs involved.

The basis for the activity of the compounds of the present invention in different types of amyloidosis is to be found in the common ultrastructural organization of amyloid fibrils despite the fact that they can be formed from a variety of widely differing proteins (see: Glenner G.G., *New England J. Med.* 1980, vol 302, p. 1283 and p. 1333).

The compounds of the present invention are characterized by an acceptable toxicity and can be used to make medicaments useful to prevent, to arrest or to slow down the formation of or to induce the degradation of amyloid deposits that are formed by different amyloidogenic proteins. Therefore, the compounds of the present invention can be used in the prevention and in the treatment of different types of amyloidotic diseases such as systemic amyloidoses and amyloidoses of the peripheral and central nervous system. Amyloidoses of the central nervous system include, for example, Alzheimer's disease, Down Syndrome, spongiform encephalopathies such as Creutzfeld-Jacob disease and the like.

In the case of Alzheimer's disease, the protein that is found in amyloid deposits is referred to as amyloid β-protein or β-amyloid protein and is generally indicated as Aβ protein. The term Aβ protein encompasses proteins of different length. In brain amyloid deposits, Aβ proteins composed of 39 to 43 amino acids are usually found. Neurodegenerative disorders such as spongiform encephalopathies are characterized by the extracellular deposition of amyloid originated from a protein referred to as prion protein (PrP).

The compounds disclosed in the present invention interfere with the aggregation of monomeric Aβ1-40 peptide stimulated by a seed of Aβ1-40 amyloid fibrils. The activity of the compounds was assessed according to the procedure reported below.

An Aβ1-40 peptide monomer stock solution was prepared by dissolving the peptide in dimethylsulfoxide at a concentration of 33.33 mg/ml. The stock solution was further diluted 11.5 times with dimethylsulfoxide. This solution was then diluted with 10 mM phosphate buffer pH 7.4 containing 150 mM sodium chloride to prepare the test solution.

To an eppendorf tube containing 47 μl of Aβ1-40 peptide monomer solution were added 3 μl of a 830 μM water solution of the test compound containing 66.4 μM, based on the Aβ1-40 monomer content, of pre-formed sonicated Aβ1-40 fibrils: the resulting solution was 20 μM in Aβ1-40 monomer, 50 μm in the test compound and contained 4 μm, based on the Aβ1-40 monomer content, of pre-formed sonicated Aβ1-40 fibrils. The aggregation was allowed to proceed for two hours at 37° C. The suspension was then centrifuged at 15000 rpm for 15 minutes at +4° C., the supernatant was collected and the Aβ1-40 monomer was quantitated by HPLC.

The activity of some representative compounds is reported in Table 1. The activity is expressed as the percent of inhibition of the aggregation of a 20 μM Aβ1-40 monomer solution stimulated by 4 μm, based on the Aβ1-40 monomer content, pre-formed sonicated Aβ1-40 fibrils.

TABLE 1

Activity of representative compounds in the seed-triggered aggregation of AB1-40 peptide monomer.

| COMPOUND | % INHIBITION |
|---|---|
| 1d | 33.7 |
| 1i | 31.7 |
| 1j | 49.2 |

The compounds of the present invention can be used to make medicaments useful to prevent, to arrest or to slow down the formation or to induce the degradation of amyloid deposits that are formed by different amyloidogenic proteins. Therefore, the compounds of the present invention can be used in the prevention and in the treatment of different types of amyloidosis.

The present invention provides a pharmaceutical composition comprising a compound of formula 1 or a pharmaceutically acceptable salt thereof, as active ingredient, in association with a pharmaceutically acceptable carrier, excipient or other additive, if necessary. Also provided is a compound of formula 1, as defined above, or a pharmaceutically acceptable salt thereof, for use in the treatment of the human or animal body. Further, the present invention provides the use of a compound of formula 1, or a pharmaceutically acceptable salt thereof, in the manufacture of a medicament for use in the treatment of an amyloidosis disease.

The pharmaceutical composition containing a compound of formula 1 or salts thereof may be prepared in a conventional way by employing conventional non-toxic pharmaceutical carriers or diluents in a variety of dosage forms and ways of administration.

In particular, the compounds of formula 1 can be administered:

A) orally, for example, as tablets, troches, lozenges, aqueous or oily suspension, dispersible powders or granules, emulsions, hard or soft capsules, or syrups or elixirs. Compositions intended for oral use may be prepared according to any method known in the art for the manifacture of pharmaceutical compositions and such composition may contain one or more agents selected from the group consisting of sweetening agents, flavouring agents, coloring and preserving agents in order to provide elegant and palatable preparations.

Tablets contain the active ingredient in admixture with non-toxic pharmaceutically acceptable eccipients which are suitable for the manifacture of tablets. These excipient may be, for example, inert diluents, such as calcium carbonate, sodium carbonate, lactose, calcium phosphate or sodium phosphate; granulating and disintegrating agents, for example maize starch or alginic acid; binding agents, for example maize starch, gelatin or acacia, and lubrificating agents, for example magnesium stearate or stearic acid or talc. The tablets may be uncoated or they may be coated by known techniques to delay disintegration and absorption in the gastrointestinal tract and thereby provide a sustained action over a longer period. For example, a time delay material such glyceryl monostearate or glyceryl distearate may be employed.

Formulations for oral use may also be presented as hard gelatin capsules wherein the active ingredient is mixed with an inert solid diluent, for example calcium carbonate, calcium phosphate or kaolin, or soft gelatin capsules wherein the active ingredient is mixed with water or an oil medium, for example peanut oil, liquid paraffin or olive oil. Aqueous suspensions contain the active materials in admixture with excipients suitable for the manifacture of aqueous suspensions. Such excipients are suspending agents, for example sodium carboxymethylcellulose, methylcellulose, hydroxypropylmethyl cellulose, sodium alginate, polyvinylpyrrolidone, gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxyacetamol, or condensation products of ethylene oxide with partial esters derived from fatty acids and an hexitol such as polyoxyethylene sorbitol monooleate, or condensation products of ethylene oxide with partial esters derived from fatty acids and a hexitol anhydrides, for example polyoxysorbitan monooleate. The said aqueous suspension may also contain one or more preservatives, for example ethyl or n-propyl p-hydroxybenzoate, one or more coloring agents, one or more flavouring agents, one or more sweetening agents such as sucrose or saccharin.

Oily suspension may be formulated by suspending the active ingredient in a vegetable oil, for example arachis oil, olive oil, seseme oil, coconut oil or in a mineral oil such as liquid paraffin. The oily suspension may contain a thickening agent, for example beewax, hard paraffin or cetyl alcohol. Sweetening agents, such as those set forth above, and flavoring agents may be added to provide a palatable oral preparation.

These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and coloring agents may also be present.

The pharmaceutical compositions of the invention may also be in the form of oil-in-water emulsions.

The oily phase may be a vegetable oil, for example olive oil or arachis oil, or a mineral oil, for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents. Syrups and elixirs may be formulated with sweetening agents, for example glycerol, sorbitol or sucrose. Such formulations may also contain a demulcent, a preservative, coloring and flavoring agents.

B) Parenterally, either subcutaneously or intravenously or intramuscularly, or intrasternally, or by infusion techniques. The pharmaceutical compositions may be in the form of a sterile injectable aqueous or olagenous suspensions.

This suspensions may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example a solution in 1,3-butanediol. Among the acceptable vehicles and solvents that may be employed are water, Ringer's solution and isotonic sodium chloride solution. In addition, sterile fixed oils are conventionally employed as a solvent or suspending medium.

For this purpose any bland fixed oils may be conventionally employed including synthetic mono or diglycerides. In addition fatty acids such as oleic acid find use in the preparation of injectables.

The present invention further provides a method of treating a human or animal, e.g. a mammal, suffering from or susceptible to an amyloidotic disease, which method comprises administering thereto a non-toxic and therapeutically effective amount of a compound of the formula 1 or a pharmaceutically acceptable salt thereof.

A typically daily dose is from about 0.1 to about 50 mg per 30 Kg of body weight, according to the activity of the specific compound, the age, weight and conditions of the subject to be treated, the type and the severity of the disease, and the frequency and route of administration; preferably, daily dosage levels are in the range of 5 mg to 2 g. The amount of active ingredient that may be combined with the carrier materials to produce a single dosage form will vary depending upon the host treated and the particular mode of administration. For example, a formulation intended for oral may contain from 5 to about 95% of the total composition. Dosage unit forms will generally contain between from about 5 mg to about 500 mg of the active ingredient.

The following examples illustrate the invention without limiting it.

EXAMPLE 1

9-Deacetyl-9-(2-aminothiazol-4-yl)-daunomycinone (1a)

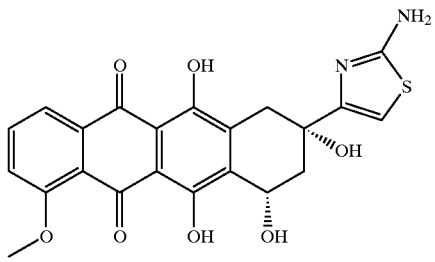

0.5 g (1.05 mmol) of 14-bromodaunomycinone 2 ($R_1$=$OCH_3$; $R_2$=$R_3$=OH) was suspended in 100 ml of a 1:1 mixture (by volume) of ethanol and dioxane and 76 mg (1.26 mmol) of thiourea were added. The reaction was kept at room temperature for 6 hours. The solvent was then removed under reduced pressure, the residue was dissolved in methylene chloride and washed with a diluted solution of ammonium hydrate and then with water. The organic phase was dried over anhydrous sodium sulphate, then concentrated and crystallized from ethylacetate to afford 0.31 g (60% yield of the title compound.

FAB-MS, m/z: 455 $[M+H]^+$; 437 $[M+H-H_2O]^+$; 421 $[M+H-2H_2O]^+$; $^1$H-NMR (200 MHz, DMSO-$d_6$) δ: 2.20 (m, 2H, C$\underline{H}_2$-8); 3.10 (m, 2H, C$\underline{H}_2$-10); 3.97 (s, 3H, OC$\underline{H}_3$); 5.03 (m, 1H, $\underline{H}$-7); 5.30 (d, J=7.7 Hz, 1H, O$\underline{H}$-7); 5.78 (S, 1H, O$\underline{H}$-9); 6.44 (s, 1H, thiazole proton); 6.89 (broad signal, 2H, N$\underline{H}_2$); 7.62 (m, 1H, $\underline{H}$-3); 7.88 (m, 2H, $\underline{H}$-1 +$\underline{H}$-2); 13.24 (broad signal, 1H, O$\underline{H}$-11); 13.96 (broad signal, 1H, O$\underline{H}$-6).

The compound was then converted into the corresponding hydrochloride by treatment with methanol saturated with gaseous hydrogen chloride and then crystallized from acetone (m.p.>270° C.

EXAMPLE 2

9-Deacetyl-9-(2-ethylamino-thiazol-4-yl)-daunomycinone (1b)

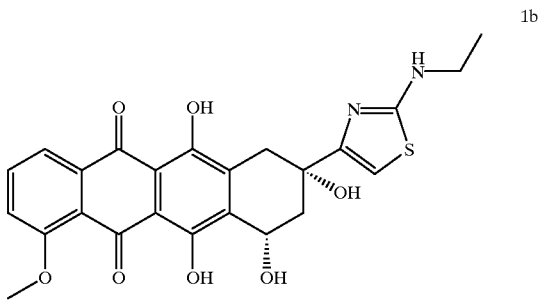

Operating as in example 1, but employing N-ethylthiourea (prepared as described in the literature; m.p. 101–103° C.) instead of thiourea, the title compound was obtained in 93% yield.

ESI-MS, m/z: 483 $[M+H]^+$; 465 $[M+H-H_2O]^+$; 447 $[M+H-H_2O]^+$. $^1$H-NMR (200MHz, DMSO-$d_6$) δ: 1.12 (t, J=7.1 Hz, 3H, $CH_2C\underline{H}_3$); 2.21 (m, 2H, C$\underline{H}_2$-8); 3.13 (s, 2H, C$\underline{H}_2$-10); 3.16 (m, 2H, C$\underline{H}_2CH_3$); 3.98 (s, 3H, OC$\underline{H}_3$); 5.04 (m, 1H, $\underline{H}$-7); 5.32 (d, J=7.6 Hz, 1H, O$\underline{H}$-7); 5.81 (s, 1H, O$\underline{H}$-9); 6.48 (s, 1H, thiazole proton); 7.49 (t, J=5.6 Hz, 1H, N$\underline{H}CH_2$); 7.63 (m, 1H, $\underline{H}$-3); 7.89 (m, 2H, $\underline{H}$-1+$\underline{H}$-2); 13.26 (broad signal, 1H, O$\underline{H}$-11); 13.98 (broad signal, 1H, O$\underline{H}$-6).

Compound 1b was then converted into the corresponding hydrochloride, as described in example 1 (m.p. 242–244° C.).

EXAMPLE 3

9-Deacetyl-9-(2-diethylamino-thiazol-4-yl)-daunomycinone (1c)

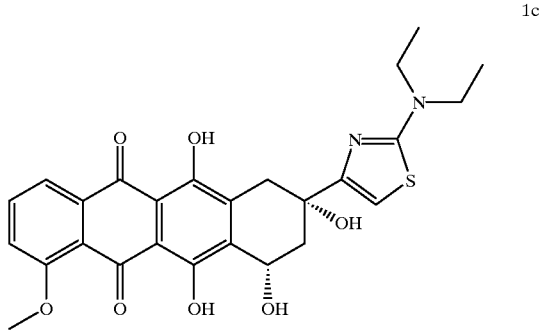

Operating as in example 1, but employing N,N diethylthiourea (prepared as described in the literature; m.p. 99–101° C.), the title compound was obtained in 83% yield.

ESI-MS, m/z: 511 $[M+H]^+$; 493 $[M+H-H_2O]^+$; 475 $[M+H-2H_2O]^+$. $^1$H-NMR (400 MHz, DMSO-$d_6$) δ: 1.12 (t,

J=7.3 Hz, 6H, CH₂C*H*₃); 2.16 (d, J=14.1 Hz, 1H, *H*-8eq); 2.26 (dd, J=4.7, 14.1 Hz, 1H, *H*-8ax); 3.12 (m, 2H, C*H*₂-10); 3.39 (q, J=7.3 Hz, 4H, C*H*₂CH₃); 3.97 (s, 3H, OC*H*₃); 5.01 (m, 1H, *H*-7); 5.29 (d, J=7.7 Hz, 1H, O*H*-7); 5.79 (s, 1H, O*H*-9); 6.54 (s, 1H, *H*-3); 7.86 (m, 2H, *H*-1+*H*-2); 13.20 (broad signal, 1H, O*H*-11); 13.95 (broad signal, 1H, O*H*-6).

Compound 1c was then converted into the corresponding hydrochloride as described in example 1 (m.p.>270° C.).

EXAMPLE 4

9-Deacetyl-9-[2-(2-dimethylamino ethylamino)-thiazol-4-yl]-daunomycinone (1d)

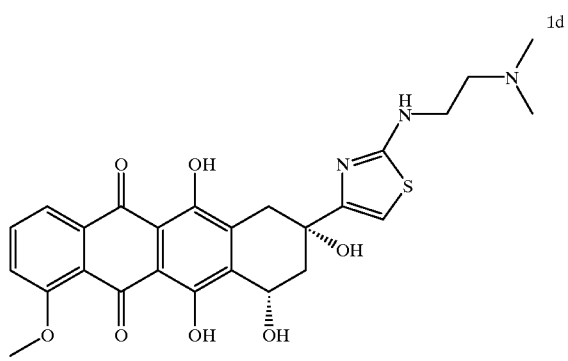

1d

Operating as in example 1, but employing N-(2,2-dimethylaminoethyl)-thiourea (prepared as described in the literature; m.p. 71–73° C.), the title compound was obtained in 76% yield.

ESI-MS, m/z: 526 [M+H]⁺; 508 [M+H-H₂O]⁺; 490 [M+H-2H₂O]⁺. ¹H-NMR (400 MHz, DMSO-d₆) δ: 2.13 (s, 6H, N(C*H*₃)₂); 2.20 (m, 2H, C*H*₂-8); 2.38 (t, J=6.8 Hz, 2H, C*H*₂N(CH₃)₂); 3.11 (s, 2H, C*H*₂-10); 3.25 (m, 2H, NHC*H*₂); 3.97 (s, 3H, OC*H*₃); 5.02 (m, 1H, *H*-7); 5.30 (d, J=7.7 Hz, 1H, O*H*-7); 5.78 (s, 1H, thiazole proton); 7.40 (t, J=5.5 Hz, 1H, N*H*CH₂); 7.61 (m, 1H, *H*-3); 7.86 (m, 1H, *H*-1+*H*-2); 13.20 (broad signal, 1H, O*H*-11); 13.95 (broad signal, 1H, O*H*-6).

Compound 1d was then converted into the corresponding dihydrochloride as described in example 1 (m.p. 270–272° C.).

EXAMPLE 5

9-Deacetyl-9-[2-(3-dimethylamino propylamino)-thiazol-4-yl]-daunomycinone (1e)

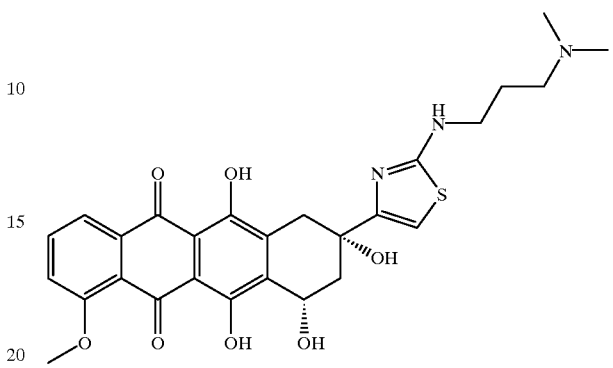

1e

Operating as described in example 1, but employing N-(3,3-dimethylaminopropyl)-thiourea (prepared as described in the literature; m.p. 64–66° C.), the title compound was obtained in 60% yield.

FAB-MS, m/z: 540 [M+H]⁺; 522 [M+H-H₂O]⁺; 504 [M+H-2H₂O]⁺. ¹R-NMR (200 MHz, DMSO-d₆) δ: 1.64 (m, 2H, NHCH₂C*H*₂CH₂NMe₂); 2.08 (s, 6H, N(C*H*₃)₂); 2.23 (m, 4H, C*H*₂-8+C*H*₂NMe₂); 3.11 (s, 2H, C*H*₂-10); 3.15 (m, 2H, NHC*H*₂); 3.97 (s, 3H, OC*H*₃); 5.02 (m, 1H, *H*-7); 5.30 (broad signal, 1H, O*H*-7); 5.77 (s, 1H, O*H*-9); 6.47 (s, 1H, thiazole proton); 7.49 (t, J=5.5 Hz, 1H, N*H*CH₂); 7.61 (m, 1H, *H*-3); 7.86 (m, 2H, *H*-1+*H*-2); 13.30, 13.80 (two broad signals, 2H, O*H*-11+O*H*-6).

Compound 1e was then converted into the corresponding dihydrochloride as described in example 1 (m.p. 229–231° C.).

EXAMPLE 6

9-Deacetyl-9-[2-(morpholin-4-yl)-thiazol-4-yl]-daunomycinone (1f)

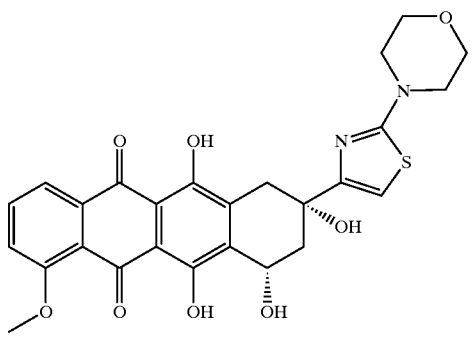

1f

Operating as in example 1, but employing 4-thiocarbamoyl-morpholine (prepared as described in the literature; m.p. 177–179° C.), the title compound was obtained in 75% yield.

ESI-MS, m/z: 525 [M+H]$^+$; 507 [M+H-H$_2$O]$^+$; 489 [M+H-2H$_2$O]$^+$. $^1$H-NMR (200 MHz, DMSO-d$_6$) δ: 2.20 (m, 2H, C$\underline{H}_{2\text{-}8}$); 3.12 (s, 2H, C$\underline{H}_{2\text{-}10}$); 3.34 (m, 4H, C$\underline{H}_2$N$\underline{H}$C$_2$); 3.69 (m, 4H, C$\underline{H}_2$OC$\underline{H}_2$); 3.97 (S. 3H, OC$\underline{H}_3$); 5.02 (m, 1H, $\underline{H}$-7); 5.33 (d, J=7.6 Hz, 1H, O$\underline{H}$-7); 5.87 (s, 1H, O$\underline{H}$-9); 6.74 (s, 1H, thiazole proton); 7.62 (m, 1H, $\underline{H}$-3); 7.86 (m, 2H, $\underline{H}$-1+$\underline{H}$-2); 13.24 (s, 1H, O$\underline{H}$-11); 13.95 (s, 1H, O$\underline{H}$-6).

Compound 1f was then converted into the corresponding hydrochloride as described in example 1 (m.p.>270° C.).

EXAMPLE 7

9-Deacetyl-9-[2-(morpholin-4-yl)-thiazol-4-yl]-daunomycinone (1g)

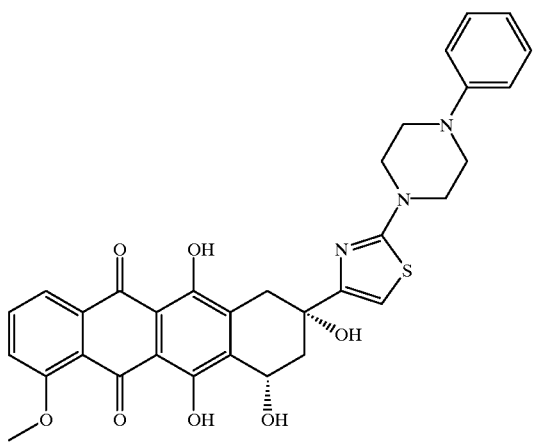

1g

Operating as in example 1, but employing 1-thiocarbamoyl-4-phenylpiperazine (prepared as described in the literature; m.p. 195–197° C.), the title compound was obtained in 52% yield (m.p. 135–137° C.).

ESI-MS, m/z: 600 [M+H]$^+$; 582 [M+H-H$_2$O]$^+$; 564 [M+H-2H$_2$O]$^+$. $^1$H-NMR (200 MHz, DMSO-d$_6$) δ: 2.22 (m, 2H, C$\underline{H}_2$-8); 3.16 (s, 2H, C$\underline{H}_2$-10); 3.24, 3.51 (two multiplets, 8H, piperazine methylenes); 3.99 (s, 3H, OC$\underline{H}_3$); 5.08 (m, 1H, $\underline{H}$-7); 5.35 (d, J=7.8 Hz, O$\underline{H}$-7); 5.89 (s, 1H, O$\underline{H}$-9); 6.75 (s, 1H, thiazole proton); 6.80 (m, 1H, phenyl para-H); 6.99 (m, 2H, phenyl ortho-H); 7.22 (m, 2H, phenyl meta-H); 7.65 (m, 1H, $\underline{H}$-3); 7.92 (m, 2H, H-1+H-2); 13.29 (s, 1H, O$\underline{H}$-11); 14.00 (s, 1H, O$\underline{H}$-6).

EXAMPLE 8

9-Deacetyl-9-[2-(4-methyl-piperazin-1-yl)-thiazol-4-yl]-daunomycinone (1h)

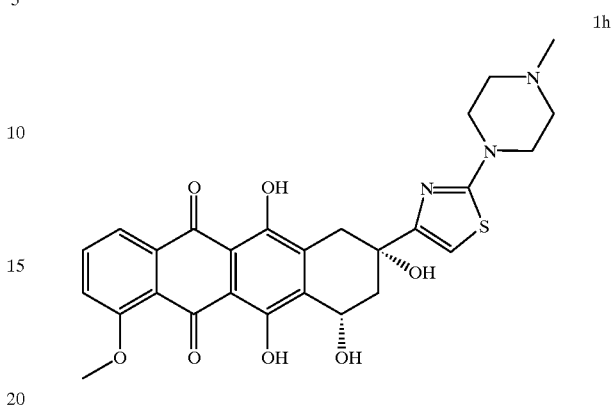

1h

Operating as in example 1, but employing 1-thiocarbamoyl-4-methylpiperazine (prepared as described in the literature; m.p. 207–209° C.), the title compound was obtained in 45% yield (m.p. 145–151° C.).

ESI-MS, m/z: 538 [M+H]$^+$; 520 [M+H-H$_2$O]$^+$; 502 [M+H-2H$_2$O]$^+$. 1H-NMR (400 MHz, DMSO-d$_6$) δ: 2.20 (m, 2H, C$\underline{H}_2$-8); 2.20 (s, 3H, NC$\underline{H}_3$); 2.40 (m, 4H, Me—N(C$\underline{H}_2$)$_2$); 3.10 (s, 2H, C$\underline{H}_2$-10); 3.36 (m, 4H, thiazole-N(C$\underline{H}_2$)$_2$); 3.95 (s, 3H, OC$\underline{H}_3$); 4.99 (m, 1H, $\underline{H}$-7); 5.29 (d, J=7.7 Hz, 1H, O$\underline{H}$-7); 5.81 (S, 1H, O$\underline{H}$-9); 6.70 (s, 1H, thiazole proton); 7.56 (m, 1H, $\underline{H}$-3); 7.82 (m, 1H, $\underline{H}$-1 +$\underline{H}$-2); 13.20 (s, 1H, O$\underline{H}$-11); 13.90 (s, 1H, O$\underline{H}$-6).

EXAMPLE 9

7-Deoxy-9-deacetyl-9-[2-(4-methyl-piperazin-1-yl)-thiazol-4-yl]-daunomycinone (1I)

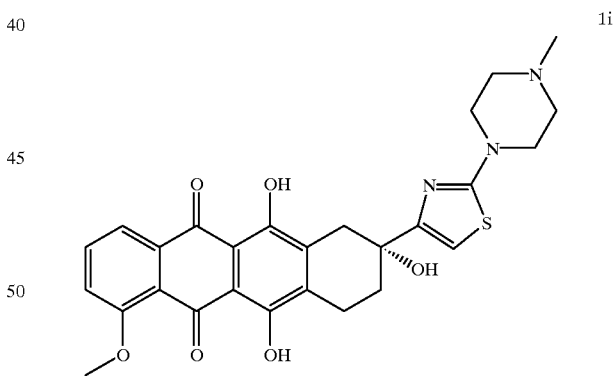

1i

Compound 1h (0.5 g, 0.93 mmol) was dissolved in 15 ml of dimethylformamide under nitrogen and sodium dithionite hydrate (0.71 g, 3.7 mmol ) dissolved in 15 ml of water was added. The reaction was kept at room temperature for 48 hours. The solvent was then removed under reduced pressure; the residue was redissolved in methylene chloride and washed with a diluted solution of ammonium hydrate and then with water. The organic layer was dried on anhydrous sodium sulphate, then concentrated and crystallized from diethyl ether to give 0.39 g (81% yield) of the title compound.

ESI-MS, m/z: 522 [M+H]$^+$; 504 [M+H-H$_2$O $^+$. $^1$H-NMR (200 MHz, CDCl$_3$) δ: 2.17 (m, 2H, CH2-8); 2.35 (s, 3H, NCH$_3$); 2.53 (m, 4H, Me-N(CH$_2$)$_2$); 3.00 (m, 2H, CH2-7); 3.19 (s, 2H; CH$_2$-10); 3.51 (m, 4H, thiazole-N(CH$_2$)$_2$); 4.08 (s, 3H, OCH$_3$); 6.35 (s, 1H, thiazole proton); 7.36 (dd, J=1.2, 8.5 Hz, 1H, H-3); 7.75 (dd, J=7.8, 8.5 Hz, 1H, H-2); 8.04 (dd, J=1.2, 7.8 Hz, 1H, H-1); 13.53 (s, 1H, OH-11); 13.89 (s, 1H, OH-6).

Compound 1i was then converted into the corresponding dihydrochloride as described in example 1 (m.p. 227–229° C.).

EXAMPLE 10

7-Deoxy-7-(4-morpholinyl)-9-deacetyl-9-[2-(4-methyl-perazin-1-yl)-thiazol-4-yl]-daunomycinone (1j)

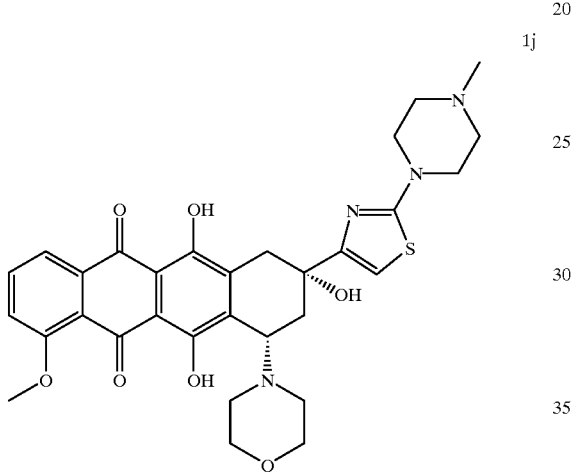

Compound 1h (0.5 g, 0.93 mmol) and triethylamine (1.1 ml, 7.44 mmol) were dissolved in 20 ml of methylene chloride and ethylchloroformate (0.75 ml, 7.44 mmol) in methylene chloride was added. After 5 hours at room temperature the mixture was washed with water, the organic layer dried over anhydrous sodium sulphate and then evaporated to dryness. Without further purification the corresponding tricarbonate 8 (R$_1$=OCH$_3$, R$_3$=OH; R$_4$=2-(4-methyl-piperazin-1-yl)-thiazol-4-yl) was redissolved in methylene chloride and morpholine (0.81 ml, 9.3 mmol) was added. After 48 hours under stirring at room temperature the mixture was washed with water, the organic layer dried over anhydrous sodium sulphate and evaporated to obtain a residue which was chromatographed on silica gel (eluant: cyclohexane/acetone 9:1) to give 0.11 g (20% yield) of the title compound.

ESI-MS, m/z: 607 (M+H]$^+$; 520 [M+H-morpholine]$^+$; 502 [M+H-morpholine-H$_2$O]$^+$. $^1$H-NMR (200 MHz, CDCl$_3$) δ: 2.20 (dd, J=3.4, 14.4 Hz, 1H, H-8ax); 2.33 (s, 3H, NCH$_3$); 2.35 (m, 1H, H-8eq); 2.49 (m, 4H, Me—N(CH$_2$)$_2$); 2.50, 3.03 (2 m, 4H, morpholine N(CH$_2$)$_2$); 3.34 (d, J=20.2 Hz, 1H, H-10eq); 3.45 (d, J=20.2 Hz, 1H, H-10ax); 3.46 (m, 4H, thiazole-N(CH$_2$)$_2$); 3.66 (m, 4H, morpholine O(CH$_2$)$_2$); 4.10 (s, 3H, OCH$_3$); 4.35 (m, 1H, H-7); 6.69 (s, 1H, thiazole proton); 7.39 (dd, J=1.0, 8.5 Hz, 1H, H-3); 7.78 (dd, J=7.8, 8.5 Hz, 1H, H-2); 8.04 (dd, J=1.0, 7.8 Hz, 1H, H-1); 8.50 (broad signal, 1H, OH-9); 13.35 (s, 1H, OH-11); 14.19 (s, 1H, OH-6).

Compound 1j was then converted into the corresponding trihydrochloride as described in example 1 (m.p. 180–182° C.).

Operating as described in example 1, the following compounds may also be prepared.

EXAMPLE 11

9-Deacetyl-9-[2-(piperidin-1-yl)-thiazol-4-yl]-daunomycinone (1k)

EXAMPLE 12

9-Deacetyl-9-[2-(1,2,3,6-tetrahydropyridin-1-yl)-thiazol-4-yl]-daunomycinone (1k)

EXAMPLE 13

9-Deacetyl-9-[2-(pyrrolidin-1-yl)-thiazol-4-yl]-daunomycinone (1l)

Operating as described in example 10, the following compounds may also be prepared.

EXAMPLE 14

7-Deoxy-7-ethylamino-9-deacetyl-9-[2-(4-methyl-piperazin-1-yl)-thiazol-4-yl]-daunomycinone (1m)

EXAMPLE 15

7-Deoxy-7-diethylamino-9-deacetyl-9-[2-(4-methyl-piperazin-1-yl)-thiazol-4-yl]-daunomycinone (1n)

EXAMPLE 16

7-Deoxy-7-(3,3-dimethylamino propylamino)-9-deacetyl-9-[2-(4-methyl-piperazin-1-yl)-thiazol-4-yl]-daunomycinone (1o)

EXAMPLE 17

7-Deoxy-7-(pyrrolidin-1-yl)-9-deacetyl-9-[2-(4-methyl-piperazin-1-yl)-thiazol-4-yl]-daunomycinone (1p)

EXAMPLE 18

7-Deoxy-7-(piperidin-1-yl)-9-deacetyl-9-[2-(4-methyl-piperazin-1-yl)-thiazol-4-yl]-daunomycinone (1g)

EXAMPLE 19

7-Deoxy-7-(1,2,3,6-tetrahydro-pyridin-1-yl)-9-deacetyl-9-[2-(4-methyl-piperazin-1-yl)thiazol-4-yl]-daunomycinone (1r)

EXAMPLE 20

7-Deoxy-7-(4-methyl-piperazin-1-yl)-9-deacetyl-9-[2-(4-methyl-piperazin-1-yl)-thiazol-4-yl]-daunomycinone (1s)

EXAMPLE 21

Tablets containing the following ingredients may be produced in a conventional manner:

| Ingredient | Per Tablet |
| --- | --- |
| Compound 1 | 25.0 mg |
| Lactose | 125.0 mg |
| Maize starch | 75.0 mg |
| Talc | 4.0 mg |
| Magnesium stearate | 1.0 mg |

Total weight 230.0 mg

EXAMPLE 22

Capsules containing the following ingredients may be produced in a conventional manner:

| Ingredient | Per capsule |
| --- | --- |
| Compound 1 | 50.0 mg |
| Lactose | 165.0 mg |
| Maize starch | 20.0 mg |
| Talc | 5.0 mg |
| Capsule weight | 240.0 mg |

What is claimed is:

1. A compound of formula 1

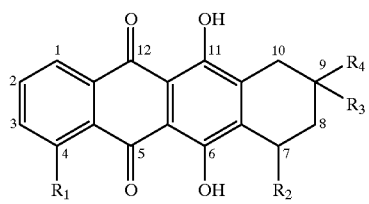

wherein:

$R_1$ is selected from:
   hydrogen,
   hydroxy,
   a group of formula $OR_5$ wherein $R_5$ is $C_1$–$C_6$ alkyl, $C_2$–$C_6$ alkenyl or $C_3$–$C_8$ cycloalkyl,
   halogen and
   amino which may be unsubstituted or mono or disubstituted by $C_1$–$C_6$ alkyl, $C_2$–$C_6$ alkenyl, aralkyl, acyl or trifluoroacetyl;

$R_2$ is selected from:
   hydrogen,
   hydroxy and
   a group $NR_6R_7$ wherein $R_6$ and $R_7$ independently represent hydrogen, an optionally substituted $C_1$–$C_6$ alkyl, $C_2$–$C_6$ alkenyl, $C_3$–$C_8$ cycloalkyl or, taken together with the nitrogen atom, represent an optionally substituted $C_3$–$C_8$ heterocyclic ring;

$R_3$ is selected from:
   hydrogen and
   hydroxy;

$R_4$ is an heterocycle of formula A:

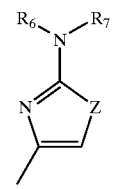

wherein Z represents sulfur or nitrogen and $R_6$ and $R_7$ are as defined above and the pharmaceutically acceptable salt thereof.

2. A compound according to claim 1, wherein $R_1$ is selected from the group consisting of hydrogen, hydroxy and methoxy;

$R_2$ is selected from the group consisting of hydrogen, hydroxy and a group of formula $NR_6R_7$, wherein one or both of $R_6$ and $R_7$ represent hydrogen, methyl, ethyl, propyl, butyl, dimethylaminoethyl, dimethylaminopropyl, or taken together represent 4-morpholinyl, 4methylpiperazinyl, 4-phenylpiperazinyl, 1-piperidinyl, 1-pyrrolidinyl, or 1,2,3,6-tetrahydropyridinyl;

$R_3$ is selected from the group consisting of hydrogen and hydroxy;

$R_4$ is a 2-substituted thiazolyl or imidazolyl system as defined in claim 1, or the pharmaceutically acceptable salt thereof.

3. A compound according to claim 1, which is 7-deoxy-7-(4-morpholinyl)-9-deacetyl-9-[2-(4-methyl-piperazin-1-yl)-thiazol-4-yl]-daunomycinone, or a pharmaceutically acceptable salt thereof.

4. A process for preparing a compound of formula 1 as defined in claim 1, comprising:

(a) reacting a compound of formula 2,

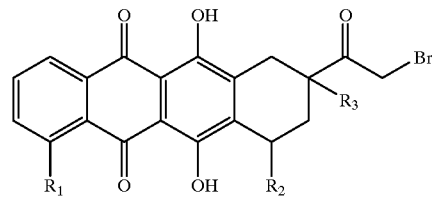

wherein $R_1$ and $R_3$ are as defined in claim 1 and $R_2$ is hydrogen or hydroxy, with a compound of formula 3 or 7, wherein $R_6$ and $R_7$ are as defined in claim 1; and
   optionally hydrolyzing the resultant compound; and (b) reacting the resultant compound of formula 1 by alkylation, reduction, condensation or substitution, and/or optionally converting the resultant compound into a pharmaceutically acceptable salt.

5. A process according to claim 4 for preparing a compound of formula 1 wherein Z is sulfur, wherein in step (a) a compound of formula 2 is reacted with a compound of formula 3 in an organic solvent for a period of 1 to 24 hours at a temperature ranging from room temperature to 100° C.

6. A process according to claim 4 for preparing a compound of formula 1 wherein Z is nitrogen, wherein in step (a) a compound of formula 2 is reacted with a compound of formula 7 in an organic solvent for a period of 1 to 24 hours at a temperature ranging from room temperature to 100° C., and the resulting intermediate 2-acetylamino-imidazole of formula 8

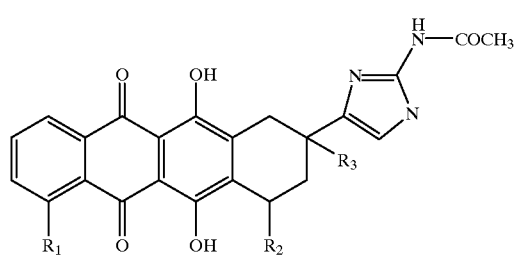

wherein:

$R_1$ is selected from the group consisting of
hydrogen,
hydroxy,
a group of formula $OR_5$ wherein $R_5$ is $C_1$–$C_6$ allyl, $C_2$–$C_6$ alkenyl or $C_3$–$C_8$ cycloalkyl, halogen and amino which may be unsubstituted or mono or disubstituted by $C_1$–$C_6$ alkyl, $C_2$–$C_6$ alkenyl, aralkyl, acyl or trifluoroacetyl;

$R_2$ is selected from the group consisting of
hydrogen,
hydroxy and
a group $NR_6R_7$ wherein $R_6$ and $R_7$ independently represent hydrogen, an optionally substituted $C_1$–$C_6$ alky, $C_2$–$C_6$ alkenyl, $C_3$–$C_8$ cycloalkyl or, taken together with the nitrogen atom, represent an optionally substituted $C_3$–$C_8$ heterocyclic ring;

$R_3$ is selected from the group consisting of
hydrogen and
hydroxy;

is then hydrolized.

7. A pharmaceutical composition which comprises, as active ingredient, a compound of formula 1 as defined in claim 1, or a pharmaceutically acceptable salt thereof, in admixture with a pharmaceutically acceptable carrier or diluent.

8. A method, comprising:

administering a non-toxic and effective amount of the compound of formula (I), as defined in claim 1, or a pharmaceutically acceptable salt thereof to a subject in need thereof, thereby slowing the formation of an amyloid deposit or degrading an amyloid deposit.

9. A method of treating Alzheimer's disease, spongiform encephalopathies or Down's syndrome, comprising:

administering to a subject in need thereof an effective amount of the compound of formula (I), as defined in claim 1, or a pharmaceutically acceptable salt thereof.

* * * * *

UNITED STATES PATENT AND TRADEMARK OFFICE
CERTIFICATE OF CORRECTION

PATENT NO. : 6,316,451 B1  Page 1 of 1
DATED : November 13, 2001
INVENTOR(S) : Mantegani et al.

It is certified that error appears in the above-identified patent and that said Letters Patent is hereby corrected as shown below:

Title page,
Item [75], the Inventors' information should read:
-- [75] Inventors: Sergio Mantegani; Gabriella Traquandi, both of Milan; Tiziano Bandiera, Gamboló; Jacqueline Lansen, San Vittore Olona; Mario Varasi, Milan, all of (IT) --

Item [86], the PCT information should read:
-- [86] PCT NO.: PCT/EP99/01554
§ 371 Date: Sep. 26, 2000
§ 102(e) Date: Sep. 26, 2000

Signed and Sealed this

Twenty-eighth Day of May, 2002

Attest:

Attesting Officer

JAMES E. ROGAN
Director of the United States Patent and Trademark Office